United States Patent [19]

Durrwachter et al.

[11] Patent Number: 5,292,945
[45] Date of Patent: Mar. 8, 1994

[54] PROCESS FOR PREPARING α-CHLORO-α-OXIMINO-4-HYDROXYACETOPHENONE

[75] Inventors: John R. Durrwachter, Corpus Christi; Charlet R. Lindley, Portland; Graham N. Mott, Corpus Christi, all of Tex.

[73] Assignee: Hoechst Celanese Corporation, Somerville, N.J.

[21] Appl. No.: 17,550

[22] Filed: Feb. 16, 1993

Related U.S. Application Data

[63] Continuation-in-part of Ser. No. 801,999, Dec. 3, 1991, abandoned.

[51] Int. Cl.$^5$ .............................................. C07C 53/00
[52] U.S. Cl. ............................................... 562/804
[58] Field of Search ............................... 562/804, 800

[56] References Cited

U.S. PATENT DOCUMENTS

| | | | |
|---|---|---|---|
| 2,320,234 | 4/1940 | Hartung et al. | 562/804 |
| 3,778,475 | 12/1973 | Jakob | 562/804 |
| 3,794,620 | 2/1974 | Bateman | 562/804 |
| 3,914,267 | 10/1975 | Rennie et al. | 562/804 |
| 4,910,338 | 3/1990 | Fruchey | 562/800 |

*Primary Examiner*—José G. Dees
*Assistant Examiner*—Keith MacMillan
*Attorney, Agent, or Firm*—James J. Mullen; Donald R. Cassady

[57] ABSTRACT

A process for the preparation of α-chloro-α-oximino-4-hydroxyacetophenone by reacting nitrosyl chloride with a mixture of 4-hydroxyacetophenone and a strong acid catalyst such as hydrogen chloride is disclosed. The nitrosyl chloride is introduced as a gas into the reactor to contact 4-hydroxyacetophenone and said acid catalyst dissolved in a solvent therein.

18 Claims, No Drawings

PROCESS FOR PREPARING α-CHLORO-α-OXIMINO-4-HYDROXYACETOPHENONE

RELATED APPLICATIONS

This application is a continuation-in-part of pending patent application Ser. No. 07/801,999 filed Dec. 3, 1991 now abandoned.

TECHNICAL FIELD OF THE INVENTION

The present invention relates to α-chloro-α-oximino-4-hydroxyacetophenone and, more particularly, to a method for the preparation thereof. Still more particularly, the present invention relates to a method for preparing α-chloro-α-oximino-4-hydroxyacetophenone by reacting 4-hydroxyacetophenone with nitrosyl chloride.

BACKGROUND OF THE INVENTION

The compound α-chloro-α-oximino-4-hydroxyacetophenone is a well known compound having the structural formula (Formula 1):

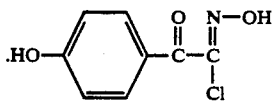

The compound is known to have good anti-bacterial and germicidal properties. Accordingly, it is used as an industrial biocide to control the growth of bacteria and microorganisms which develop in water-based media used in the manufacture of various industrial products. The discovery of the antibacterial and germicidal properties of the compound is described in British Patent No. 1,290,646.

When used as an industrial biocide, α-chloro-α-oximino-4-hydroxyacetophenone is used in association with a suitable vehicle. Suitable vehicles include water, alcohol, hydrocarbons and other organic solvents as well as mineral, animal and vegetable oils. The compositions typically contain about five (5) to about twenty (20) percent by weight of the active ingredient.

Several methods have been employed in the past for the preparation of α-chloro-α-oximino-4-hydroxyacetophenone. Levin et al. 7 *Journal of Organic Chemistry*, 408 (1942), discloses the preparation of the compound by reacting hydroxyphenacyl chloride with isopropyl nitrite in the presence of hydrogen chloride. One disadvantage of that method is that hydroxyphenacyl chloride is expensive and difficult to handle. Furthermore, hydroxyphenacyl chloride is a strong lachrymator and causes severe dermatitis.

U.S. Pat. No. 4,910,338 discloses the preparation of α-chloro-α-oximino-4-hydroxyacetophenone by reacting 4-hydroxyacetophenone with an alkyl nitrite and hydrogen chloride wherein the amount of hydrogen chloride is carefully controlled to limit the amount thereof to about 0.1 to six moles of hydrogen chloride per mole of 4-hydroxyacetophenone until at least one equivalent of the alkyl nitrite is reacted. Subsequent to the reaction of the one equivalent of alkyl nitrite, at least one mole of hydrogen chloride per mole of initially charged 4-hydroxyacetophenone is added to the reaction medium. One disadvantage of that process is that it utilizes alkyl nitrites. The handling of those compounds is undesirable because they are potential explosives. Furthermore, another disadvantage of that process is that it generates alcohols because of the presence of the isopropyl nitrite. The isopropyl alcohol causes the generation of undesirable byproducts such as p-hydroxyphenylglyoxal acetals.

In U.S. Pat. No. 3,794,620 there is disclosed a process for the preparation of a general class of aromatic carbonyl hydroxamoyl chlorides by the reaction of aromatic acetyl derivatives with nitrosyl chloride. These chlorides are alleged to be useful as cross-linking, chain-extending, and/or capping agents for unsaturated polymers or polymers containing mercaptan groups. One of the disadvantages of this process is the fact that the reaction temperatures in the overall reaction medium increase substantially and in an uncontrolled manner.

The present invention discloses a process which substantially reduces the difficulties of the prior art processes. The process utilizes starting materials which are more economical than the starting material of the prior art processes, eliminates the handling of potentially explosive material such as alkyl nitrites, reduces the formation of undesirable by-products, and substantially reduces and controls the reaction temperatures.

These and other objects and advantages of the present invention will become apparent from the following description.

SUMMARY OF THE INVENTION

A process for the preparation of α-chloro-α-oximino-4-hydroxyacetophenone is disclosed by reacting 4-hydroxyacetophenone with nitrosyl chloride. The 4-hydroxyacetophenone is charged with a solvent to a reactor. The nitrosyl chloride which is generated in another reactor or which is available commercially is introduced as a gas into the reactor. The reaction is carried out at a temperature in the range of about 0° C. to about 20° C. at subatmospheric or slightly above atmospheric conditions. As a critical feature in the present invention, a strong acid catalyst such as hydrogen chloride is added to the 4-hydroxyacetophenone before it is contacted with the nitrosyl chloride. Thus, in order to avoid a rapid temperature rise at its initial stage, the reaction is catalyzed by adding hydrogen chloride before any reaction takes place between the 4-hydroxyacetophenone and the nitrosyl chloride. In this manner the reaction temperature can be controlled and there is prevented any undesired or unwanted by-products, or unsafe process conditions.

The nitrosyl chloride is provided by obtaining it from commercially available sources or by preparing it by a process which is integrated with the process of the present invention so that the nitrosyl chloride can be consumed in the reaction of the present invention upon its production. An example of such process involves the generation of nitrosyl chloride by reacting aqueous sodium nitrite (NaNO$_2$) with hydrochloric acid (HCl). The 4-hydroxyacetophenone used as starting material of the present invention can be obtained by several processes which are well known in the art.

DETAILED DESCRIPTION OF THE INVENTION

According to the present invention α-chloro-α-oximino-4-hydroxyacetophenone is prepared by reacting 4-hydroxyacetophenone with nitrosyl chloride (ClNO). The reaction is stoichiometrically represented as follows (Reaction 1):

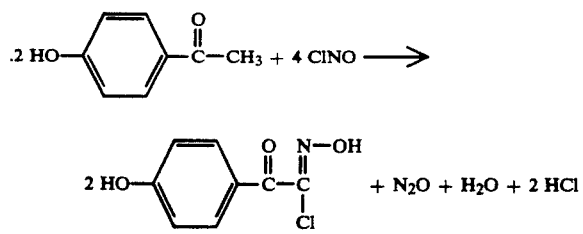

In carrying out the reaction, the 4-hydroxyacetophenone is charged to a reactor in an appropriate solvent which dissolves at least some of the 4-hydroxyacetophenone. Such solvents include, but are not limited to, ethers, halogenated hydrocarbons and nitriles. Ethers such as dimethyl ether, diisopropyl ether, tetrahydrofuran (THF), etc. are preferred. The most preferred are those ethers which are easily recoverable and less expensive such as diisopropyl ether.

The nitrosyl chloride is preferably introduced into the reactor in its gaseous state gradually by sparger or similar means. Although two moles of nitrosyl chloride are theoretically required to convert one mole of 4-hydroxyacetophenone, it is preferred that an excess of about 25 percent be used.

Because the reaction is highly exothermic, it is critical to control the reaction to avoid a rapid temperature increase in the reaction mass, especially at the initial stage thereof. In order to accomplish such control, a strong acid catalyst such as HCl, $CH_3SO_3H$, $H_2SO_4$, $HClO_4$, $HNO_3$, and the like is added to the reactor prior to the addition of the nitrosyl chloride to catalyze or speed up the reaction at the initial stage thereof to avoid the build up of nitrosyl chloride and to prevent a rapid temperature rise in the reactor. Although about one-half mole of hydrogen chloride per mole of 4-hydroxyacetophenone reactant is sufficient to accomplish such task, one mole is preferably used.

The reaction is carried out at a temperature in the range of about 0° C. to about 20° C. and, preferably, in the range of about 5° C. to about 12° C. The heat generated by the exothermic reaction is removed to maintain the reaction temperature within those ranges.

The reaction proceeds in a satisfactory manner at a pressure in the range of about 200 mmHg to slightly above atmospheric pressure. It is preferred, however, that the reaction be carried out at atmospheric pressure. Depending on several parameters of the reaction such as type of solvent, concentration of reactants, temperature and rate of removal of the heat of reaction, the reaction time required to obtain a satisfactory conversion is in the range of about thirty (30) minutes to about twenty-four (24) hours. It is preferred, however, that the reaction be carried out for about two (2) to eight (8) hours. The reaction is preferably carried out in a batch mode. A semi-batch mode or a continuous mode, however, may be utilized.

After the reaction is completed, the reaction mass is subjected to well-known separation techniques to recover the α-chloro-α-oximino-4-hydroxy-acetophenone in the solvent. In one such technique, the reaction mass is dissolved in a vehicle for the α-chloro-α-oximino-4-hydroxyacetophenone.

A suitable vehicle is poly(ethyleneglycol) of a molecular weight of about 200. Subsequently, the solvent for the 4-hydroxyacetophenone and other products of the reaction are stripped off at elevated temperatures and reduced pressure, yielding a biocide composition comprising from about five (5) to about twenty (20) percent of the product in the vehicle solution.

One of the advantages of the present invention is that the nitrosyl chloride reactant is not produced in the reaction mass but is introduced as nitrosyl chloride gas to the reaction mass from an external sourc.e As such, nitrosyl chloride may be available from commercial sources or may be produced in a separate unit by well-known methods. An example of such method involves the preparation of nitrosyl chloride by the addition of aqueous sodium nitrite ($NaNO_2$) to hydrochloric acid (HCl). The nitrosyl chloride is generated in accordance with the following reactions (Reactions 2 and 3):

 (Reaction 2)

 (Reaction 3)

An excess amount of hydrogen chloride is used to promote the conversion of HONO to nitrosyl chloride. After the reaction is finished, the excess hydrogen chloride is then neutralized with caustic. The nitrosyl chloride so generated is sparged into the reactor as described above. It is preferred that, in order to avoid accumulation of nitrosyl chloride in the manufacturing facilities, the nitrosyl chloride be consumed in the reactor carrying out Reaction 1 with 4-hydroxyacetophenone at a rate which is about the same as the rate of the generation of nitrosyl chloride by the aforesaid method.

The 4-hydroxyacetophenone may be prepared by several methods which are well-known in the art. Such methods are disclosed in U.S. Pat. Nos. 4,568,763 and 4,910,338 which are incorporated herein and made part hereof by reference.

The following examples further illustrate the invention but are not to be construed as limitations in the scope of the invention contemplated herein.

EXAMPLE 1

Preparation of a Polyethylene Glycol Solution of α-chloro-α-oximino-4-hydroxyacetophenone A nitrosyl chloride generator was set up by fitting a one liter, four-neck flask with a mechanical stirrer, an inlet for adding nitrite solution, a gas outlet and a thermocouple. Furthermore, a reactor was set up by fitting a one liter, four-neck flask with a mechanical stirrer, a gas sparger which was connected to the gas outlet from the nitrosyl chloride generator, a thermocouple, and a Dewar condenser charged with dry ice/isopropanol. The reactor head space was swept with dry nitrogen at the rate of about 0.5 standard cubic feet per hour to ensure that an explosive mixture of solvent vapor, NO, and $N_2O$ was not formed. All gases exit from the reactor via the Dewar condenser.

The reactor was charged with 4-hydroxyacetophenone (50 grams, 0.37 moles) and diisopropyl ether (375 ml, 1.0M HCL). The 4-hydroxyacetophenone was suspended in the ether. The reactor was cooled to about 5° C.

The nitrosyl chloride generator was charged with hydrochloric acid (535 grams, 30.5 percent, 4.5 moles). Aqueous $NaNO_2$ (190.4 grams, 40 percent, 1.10 moles) was introduced into the nitrosyl chloride generator with a peristaltic pump at a constant rate such that the total addition time was about six (6) hours. Nitrosyl chloride formed in the generator flowed into the reactor via the sparger. The rate of the nitrite addition together with external cooling of the reactor maintained the reactor at about 5° C. to about 10° C. Toward the end of the nitrite addition, the solids in the reactor dissolved to form a greenish brown solution.

After the addition of the nitrite was completed, the generator was sparged with nitrogen for about one (1) hour to remove residual nitrosyl chloride out of solution into the reactor. The solution in the reactor was allowed to stand overnight at room temperature. An assay of the solution (358 grams) indicated that it contained 17.1 percent by weight of α-chloro-α-oximino-4-hydroxyacetophenone (61.1 grams, 0.306 moles). This corresponds to a yield of 83 percent.

The reactor solution was transferred to a vacuum distillation system equipped with a thermocouple for monitoring the pot temperature. Solvent was removed under a vacuum of about 250 torr. When solids began to appear in the pot, the distillation was discontinued and approximately 140 grams of polyethylene glycol 200 was charged into the pot. The polyethylene glycol charged to the pot dissolved the solids which had formed, producing two liquid phases. The vacuum distillation was then continued until the diisopropyl ether was removed and the solution appeared homogeneous again. An additional amount of polyethylene glycol 200 of about 140 grams was charged into the pot. Solvent was removed under vacuum until the pot temperature reached about 85° C. The final solution of about 352 grams was yellow brown. An assay of the reactant indicated an amount of α-chloro-α-oximino-4-hydroxyacetophenone for about 16.1 weight percent (56.7 grams, 0.284 moles) corresponding to a yield of about 77 percent.

EXAMPLE 2

Preparation of
α-Chloro-α-Oximino-4-Hydroxyacetophenone in Methylene Chloride

A nitrosyl chloride generator and a reactor were set up as in Example 1. The reactor was charged with 4-hydroxyacetophenone (27.2 grams, 0.2 moles), methanesulfonic acid (1 ml) (as an acid catalyst like HCl), methylene chloride (300 ml) and ethyl acetate (25 ml). The nitrosyl chloride generator was charged with concentrated hydrochloric acid (100 ml, 1.2 moles).

After the reactor was cooled to about 0° C., the reaction was initiated by adding $NaNO_2$ (27.6 grams, 0.4 moles) to the hydrochloric acid in the nitrosyl chloride generator slowly with a metered addition funnel. The temperature of the reactor was maintained below 5° C. during the reaction. Solid precipitated out of the reaction mass of the reaction and it was filtered off. The filtrate was allowed to stand overnight at room temperature. During that time, more solids precipitated out of the reaction mass. After the solids so precipitated were filtered off, the filtrate was washed with water, dried over magnesium sulfate ($MgSO_4$) and the solvents were removed to yield a solid mass. Analysis of all solids indicated the presence of α-chloro-α-oximino-4-hydroxyacetophenone (11.6 grams, 58 micromoles) corresponding to 29 percent yield based on 4-hydroxyacetophenone.

EXAMPLE 3

A nitrosyl chloride generator was set up by fitting a one liter, three-neck round bottom flask with an overhead stirrer, a chilled water Friedreich condenser, a nitrogen gas inlet, a $NaNO_2$ inlet tube, a gas outlet and a thermocouple. A reactor was set up by fitting a one liter, four-neck round bottom flask with an overhead stirrer, a glass-frit sparger connected to the gas outlet of the nitrosyl chloride generator for flowing nitrosyl chloride to the reactor from the nitrosyl chloride generator, a thermocouple and a Dewar condenser charged with dry ice/isopropanol on the gas exit. The reactor was charged with 4-hydroxyacetophenone (50.0 grams, 0.37 moles) and isopropyl ether (270 grams, 375 ml). The reactor was cooled to about −2° C.

The nitrosyl chloride generator was charged with hydrochloric acid (37%, 410 ml). Aqueous $NaNO_2$ (207 grams, 40%, 1.2 moles) was added to the hydrochloric acid with a peristaltic pump at a constant rate for a total nitrite charge time of about one (1) hour. The nitrosyl chloride produced in the generator was sparged into the reactor as it was produced. The reactor was held at about −2° C. to about 0° C. for about one (1) hour. At the end of that period, only a small amount of the 4-hydroxyacetophenone had reacted with the hydrogen chloride and solid 4-hydroxyacetophenone was still present in the reactor. Then the reactor was allowed to warm gradually. An exothermic reaction occurred and caused a rapid temperature rise of about 15° C. to about 30° C. above ambient. After the reaction was allowed to stand for about 2 hours, an analysis of 360 grams of solution indicated the presence of α-chloro-α-oximino-4-hydroxyacetophenone therein of about 17.7 weight percent (650.7 grams, 0.319 moles) corresponding to a yield of about 87 percent.

EXAMPLE 4

Comparative

The following will demonstrate the reaction of nitrosyl chloride with 4'-hydroxyacetophenone *without* the presence of hydrogen chloride and *with* the presence of hydrogen chloride. The results are respectively shown in Table I and Table II.

Into a 1-L 3-neck flask (reactor) fitted with a dry-ice condenser, thermowell and a gas inlet dip tube was charged 4'-hydroxyacetophenone (50 g, 0.368 mole) and isopropyl ether (375 ml). In another 1-L 3-neck flask (generator) fitted with a chilled water condenser with a gas outlet on the exit, thermowell and mechanical stirrer was charged hydrochloric acid (489 ml, 31%). The reaction was initiated by pumping in $NaNO_2$ (1.2 moles, 84.0 g dissolved in 126 ml of water). The NOCl formed in the generator passed over the chilled water condenser and into the reactor via the dip tube. The reactor temperature was maintained with a salt/ice water bath.

TABLE I

| | (Without HCl) | | |
|---|---|---|---|
| Time/ Min. | g $NaNO_2$ Added | Temp, C in Reactor | Comments |
| 0 | 0.00 | −3.0 | Start |
| 2 | 7.70 | −3.1 | |
| 3 | 15.20 | −2.9 | NOCl gas to reactor |
| 10 | 25.00 | −4.0 | |
| 15 | 32.00 | −3.9 | |
| 30 | 52.40 | −3.2 | |
| 45 | 74.00 | −3.3 | |
| 60 | 91.70 | −2.7 | |
| 70 | 113.20 | −1.6 | |
| 85 | 135.00 | −2.1 | |
| 100 | 159.00 | −1.2 | NOCl refluxing in reactor |

TABLE I-continued (Without HCl)

| Time/Min. | g NaNO2 Added | Temp, C in Reactor | Comments |
|---|---|---|---|
| 115 | 183.00 | −2.2 | |
| 132 | 208.50 | −1.4 | All of NaNO2 added |
| 194 | — | −1.1 | Ice bath removed from reactor |
| 225 | — | 18.6 | All solids dissolved in reactor |
| 232 | — | 30.0 | NOCl refluxing in reactor |
| 234 | — | 31.6 | Lots of gas evolution |
| 239 | — | 40.3 | NOCl reflux slowing |
| 242 | — | 40.8 | Peak temperature |
| 303 | — | 21.3 | |

Into a 1-L 3-neck flask (reactor) fitted with a dry ice condenser, thermowell and a gas inlet dip tube was charged 4'-hydroxyacetophenone (50 g, 0.368 mole), HCl (100.3 g of 13.4% HCl in isopropyl ether, 13.44 g HCl, 0.368 mole) and isopropyl ether (195 g, 265 ml). In another 1-L 3-neck flask (generator) fitted with a chilled water condenser with a gas outlet on the exit thermowell and mechanical stirrer was charged hydrochloric acid (489 ml, 31%). The reaction was initiated by pumping in NaNO2 (1.2 moles, 84.0 g dissolved in 126 ml of water). The NOCl formed in the generator passed over the chilled water condenser and into the reactor via the dip tube. The reactor temperature was maintained with a salt/ice water bath.

TABLE II (With HCl)

| Time/Min. | g NaNO2 Added | Temp, C in Reactor | Comments |
|---|---|---|---|
| 0.00 | 0.0 | −0.7 | Start |
| 5.00 | 15.6 | −1.0 | |
| 11.00 | 21.8 | −1.2 | NOCl gas entering reactor |
| 15.00 | 26.6 | −1.2 | |
| 30.00 | 50.0 | −0.8 | |
| 45.00 | 73.3 | −0.2 | |
| 48.00 | 78.6 | −0.1 | |
| 61.00 | 100.7 | −0.1 | |
| 75.00 | 120.4 | 0.0 | Many unreacted solids (ketone) still present |
| 90.00 | | 0.5 | |
| 101.00 | 164.0 | 3.0 | More ice added to bath |
| 105.00 | 171.5 | 0.9 | |
| 120.00 | 195.0 | 2.2 | |
| 135.00 | 210.4 | 4.4 | All NaNO2 added, many solids present |
| 155.00 | — | 6.9 | Few unreacted solids left |
| 195.00 | — | 0.7 | Temp dropping off, ice bath removed |
| 203.00 | — | 8.0 | No gas evolution from reactor |
| 219.00 | — | 16.2 | No NOCl on reactor condenser |
| 225.00 | — | 17.6 | |
| 240.00 | — | 20.3 | |
| 245.00 | — | 20.6 | |
| 260.00 | — | 21.5 | |
| 300.00 | — | 20.9 | |

In Table I, where there is no added HCl reactor, there is a 40+ C° exotherm starting about 30 minutes after the ice bath is removed. Once the exotherm takes off, there is no way to control it, since all of the NOCl is in the reactor. In Table II, where HCl is added prior to the introduction of NOCl, the reaction is taking place during the addition of NOCl to the reactor. This facilitates the control of the reaction; stopping the NOCl stream will stop the reaction. As these two Tables illustrate, the addition of HCl to the reactor with the substrate ketone prior to the addition of NOCl, is essential to providing a smooth, controllable reaction. Otherwise, the reaction will be nearly dormant until enough HCl is generated either by the slow reaction of NOCl with ketone or extraneous water, or until enough HCl is carried over from the generator to catalyze the desired reaction of the ketone with NOCl. Until that point, NOCl builds up in the reactor and then reacts very rapidly with the ketone, releasing large amounts of heat in a short period of time. This sort of runaway exotherm would be very difficult and dangerous to handle on a large scale.

While the invention is described with respect to specific embodiments, modifications thereof can be made by one skilled in the art without departing from the spirit of the invention. The details of said embodiments are not to be construed a limitation except to the extent indicated in the following claim.

What is claimed is:

1. A method for preparing α-chloro-α-oximino-4-hydroxyacetophenone, comprising the step of reacting 4-hydroxyacetophenone with nitrosyl chloride, said reaction being carried out in the presence of a strong acid catalyst which was added to the 4-hydroxyacetophenone before contacting with the nitrosyl chloride.

2. The method according to claim 1 wherein an excess amount of nitrosyl chloride is used.

3. The method according to claim 1 wherein the reacting step is carried out at a temperature of from about 0° C. to about 20° C.

4. The method according to claim 3 wherein the reacting step is carried out at a temperature of from about 5° C. to about 12° C.

5. The method according to claim 1 wherein the reacting step is carried out at a pressure in the range of subatmospheric to slightly above atmospheric.

6. The method according to claim 5 wherein the reacting step is carried out at atmospheric pressure.

7. The method according to claim 1, wherein the reacting step is carried out in a reactor and the method further including the step of introducing the nitrosyl chloride into the reactor from a source separate from the reactor.

8. The method according to claim 7 further including the step of producing the nitrosyl chloride in the source.

9. The method according to claim 7 wherein the nitrosyl chloride is introduced to the reactor gradually.

10. The method according to claim 8 wherein the producing step includes the step of interacting sodium nitrite with hydrogen chloride.

11. The method according to claim 1 wherein the reacting step is carried out in the presence of a solvent.

12. The method according to claim 11 wherein the solvent is selected from the group consisting of ethers, halogenated hydrocarbons and nitriles.

13. The method according to claim 12 wherein the solvent is diisopropyl ether.

14. The method according to claim 1 wherein the nitrosyl chloride is in the vapor phase.

15. The method according to claim 1 wherein the reacting step generates heat and the method further including the step of removing the generated heat.

16. The method according to claim 1 wherein the reacting step is carried out in the absence of an alkyl nitrite.

17. A method of producing α-chloro-α-oximino-4-hydroxyacetophenone, comprising the steps of:
introducing nitrosyl chloride into a reactor from a source separate from the reactor; and contacting the nitrosyl chloride with a mixture of 4-hydroxyacetophenone and hydrogen chloride.

18. A method of producing α-chloro-α-oximino-4-hydroxyacetophenone having anti-bacterial and germicidal properties, comprising:
 a) reacting 4-hydroxyacetophenone with nitrosyl chloride in the presence of (i) a solvent which is selected from the group consisting of ethers, halogenated hydrocarbons and nitriles and (ii) hydrogen chloride which is added to the 4-hydroxyacetophenone prior to reacting with the nitrosyl chloride, and
 b) separating the produced α-chloro-α-oximino-4-hydroxyacetophenone from the reaction mass;

said reaction being conducted (i) at a temperature of from about 0° C. to about 20° C.; (ii) at a pressure in the range of sub-atmospheric to slightly above atmospheric; and (iii) in the absence of an alkyl nitrite.

* * * * *